United States Patent
Lin et al.

(10) Patent No.: US 6,429,321 B1
(45) Date of Patent: Aug. 6, 2002

(54) DEPOLYMERIZATION OF POLYTETRAHYDROFURAN DERIVATIVES

(75) Inventors: Wen-Fa Lin, Hsinchu Hsien; Chuan-Yang Liu; Jun-Yi Chen, both of Hsinchu; Long-Shuenn Jean, Chiai Hsien, all of (TW)

(73) Assignee: TCC Chemical Corporation, Chang Hua (TW)

( * ) Notice: Subject to any disclaimer, the term of this patent is extended or adjusted under 35 U.S.C. 154(b) by 0 days.

(21) Appl. No.: 09/934,324

(22) Filed: Aug. 21, 2001

(30) Foreign Application Priority Data

Jul. 11, 2001 (TW) ........................................ 90116984 A

(51) Int. Cl.$^7$ ............................................. C07D 307/38
(52) U.S. Cl. ....................................... 549/429; 549/509
(58) Field of Search .................................. 549/429, 509

(56) References Cited

FOREIGN PATENT DOCUMENTS

DE          4410685       * 10/1995

* cited by examiner

*Primary Examiner*—Bernard Dentz
(74) *Attorney, Agent, or Firm*—Darby & Darby

(57) ABSTRACT

The invention discloses a method for depolymerization of a mixture containing polytetrahydrofuran derivatives, including heating the mixture comprising polytetrahydrofuran derivatives at 100–250° C. in the presence of a β-zeolite catalyst to obtain tetrahydrofuran, whereby the tetrahydrofuran monomer can be recovered from the waste materials in the preparation of polytetramethylene ether glycols.

10 Claims, No Drawings

DEPOLYMERIZATION OF POLYTETRAHYDROFURAN DERIVATIVES

BACKGROUND OF THE INVENTION

1. Field of the Invention

The present invention relates to a method for depolymerization of polytetrahydrofuran derivatives, and particularly to the use of β-zeolite as a catalyst for converting polytetrahydrofuran derivatives to tetrahydrofuran.

2. Description of the Related Art

Polytetramethylene ether glycols (hereinafter as PTMEG), widely used as the polyol component with isocyanates to make thermoplastic polyurethanes, are obtained by the alcoholysis of polytetramethylene ether acetates (hereinafter as PTMEA).

In addition, PTMEA is prepared by polymerizing anhydrous tetrahydrofuran (hereinafter as THF) in the presence of acetic anhydride, acetic acid, and acid catalysts such as fluosulfonic acid ($HSO_3F$). In industrial production, if the catalyst exhibits-abnormal activity, or reaction system used to prepare the PTMEA is changed, it may obtain a mixing product, giving off-specification fractions composed of polymers of different molecular weight ranges. Usually, those off-specification materials are continuously alcoholyzed, separated, and purified to obtain PTMEG, which is then depolymerized to a monomer, namely to THF, and recovered. This recovery also arises whenever uncontrolled events during the synthesis lead to polymers which do not conform to the required narrow specification. Therefore, if the off-specification materials containing PTMEA are recovered directly in the preparation process, significant costs and downstream operations can be conserved.

The following prior art is directed to the process for the depolymerization of PTMEG, including:

U.S. Pat. No. 4,115,408 describes a process for depolymerizing PTMEG to THF, in which the effluent containing dissolved PTMEG is heated with sulfuric acid at the temperature high than 150° C. This process has two disadvantages in particular. First, the use of relatively concentrated acid at the temperature high than 150° C. necessarily entails substantial corrosion problems, and, secondly, the dilute aqueous sulfuric acid obtained after the depolymerization must be neutralized before it can be discharged into the sewer, thereby imposing a substantial salt load on the sewer.

U.S. Pat. No. 4,363,924 discloses the use of a bleaching earth as a catalyst. However, the activity level and life of this catalyst can be improved.

Japanese Patent No. 60-109584 discloses the use of heteropoly acid as a catalyst. Due to its high cost, use of this catalyst carries distinct economic disadvantages.

Japanese Patent No. 62-257931 discloses the use of non-crystalline $SiO_2$—$Al_2O_3$ as a catalyst. However, the activity level and life of this catalyst can be improved.

WO 95/02625 discloses the use of metal perfluoroalkylsulfonates, e.g. $(CF_3SO_3)_3Y$, as a catalyst in the presence of an accelerator. Due to the high cost, use of this catalyst carries distinct economic disadvantages.

German Patent No. DE 4410685 discloses a process for depolymerizing PTMEG, which comprises heating PTMEG in the presence of kaolin, amorphous silica, and/or X-zeolite. However, the activity level and life of these catalysts can be improved.

Japanese Patent No. 11-269262 uses the mixture of $ZrO_2$ and $SiO_2$ as a catalyst. However, the activity level of this catalyst can be improved.

All the above-cited catalyst systems are used in the depolymerization of PTMEG. No prior art teaches the depolymerization of PTMEA in the industrial process. Further, the yield and the costs of the catalysts employed in the prior art can also be improved. Therefore, there is still a need for development of a catalyst system for depolymerization of PTMEG and/or PTMEA in a more efficient manner.

SUMMARY OF THE INVENTION

The present invention, therefore, discloses the use of β-zeolite showing higher activity levels and longer life as a catalyst than those disclosed in the prior art.

The main object of the invention is to provide a method for depolymerization of a mixture comprising polytetrahydrofuran derivatives. The method comprises heating the mixture in the presence of a β-zeolite catalyst at 100–250° C. to obtain THF, whereby the THF monomers can be recovered from the waste materials in the preparation of PTMEG.

In one preferred example, the polytetrahydrofuran derivatives comprise polytetramethylene ether glycols or polytetramethylene ether acetates.

In another preferred example, the mixture comprising polytetrahydrofuran derivatives of the invention further comprises by-products or impurities such as water, sodium chloride, and sodium acetate during the process of separation and purification.

In another preferred example, the depolymerization method of the invention is carried out at 130–210° C.

DETAILED DESCRIPTION OF THE INVENTION

The equations of reacting PTMEA with or without water to obtain THF are as follows:

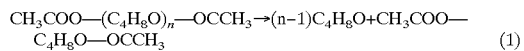

(1)

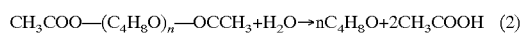

(2)

In addition, the equation of converting PTMEG to THF is as follows:

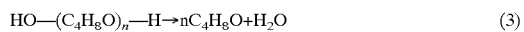

(3)

As used herein, the term "polytetrahydrofuran derivatives" includes PTMEG and PTMEA. That is, both reactants can be reacted in one process or in separate processes, according to the present invention to obtain THF monomers for recovery.

Distinct from the X-zeolite used in the process disclosed in DE 4410685, a β-zeolite is employed as a catalyst according to the present invention. β-zeolite was first synthesized in 1967, but its structure was not published until 1988. It is the only high silica zeolite having a full three-dimensional network of 12-membered rings and is somewhat like the faujasite structure. It probably has the most complex zeolite structure yet determined. Therefore, β-zeolite is different from other known zeolites in terms of structure and physical-chemical properties. Thus, β-zeolite is first used in the depolymerization of polytetrahydrofuran derivatives in the context of the invention.

In accordance with the invention, the method can be carried out in the environment of an acidic catalyst.

As used herein, the term "waste materials" includes: (1) off-specification fractions composed of PTMEG and/or PTMEA with different molecular weight ranges (e.g. molecular weight higher than the specification); (2) the PTMEG of small molecular weight cut off from the prepared PTMEG fractions; or (3) by-products or impurities such as water, sodium chloride, and sodium acetate during the process of separation and purification. Therefore, the term "mixture comprising polytetrahydrofuran derivatives" used herein, which can be depolymerized according to the invention, comprises one or more of the above components.

To carry out the depolymerization process, the PTMEG and/or PTMEA is mixed with the β-zeolite and the mixture is heated at about 100–250° C., and preferably at 130–210° C. Those skilled in the art will be aware that if higher temperatures or higher concentrations of β-zeolite are used, the reaction takes place more rapidly.

Without intending to limit it in any manner, the present invention will be further illustrated by the following examples.

EXAMPLE

Example 1

A 500 ml reaction vessel equipped with heating, a stirrer, and a descending condenser was charged with 1.5 g of β-zeolite (purchased from SUD-CHEMIE NISSAN CATALYSTS Inc.) and 250 g of PTMEG of number average molecular weight 650 (PTMEG-650). The mixture was heated at 130° C. with stirring at 200 rpm. The resulting THFs were obtained in the receiver attached to the condenser. The THF production rate was about 30 g/hr. The reactants were supplied in an intermittent manner to the 250 g of graduation on the vessel when the liquid surface was down to 200 g of graduation. The temperature was elevated for 10° C. each time when the THF production rate was decreased. The process was carried out at a final temperature of 160° C. Overall, 2290 g of THF was collected containing 3.8 wt % of $H_2O$.

Example 2

All operation parameters were the same as in example 1 except that the composition fed in the vessel included 1.5 g of β-zeolite, 91.94 wt % of PTMEG-650, 8 wt % of $H_2O$, 0.05 wt % of NaCl, and 0.01 wt % of NaOAc, and the temperature was from 130 to 170° C. Overall, 1715 g of THF was collected containing 12.3 wt % of $H_2O$.

Example 3

All operation parameters were the same as in example 1 except that the composition fed in the vessel included 1.5 g of β-zeolite and PTMEA of number average molecular weight 1782 (PTMEA-1782), and the temperature was from 120 to 210° C. Overall, 1062 g of THF was collected with 98.7% purity.

Example 4

All operation parameters were the same as in example 1 except that the composition fed in the vessel included 1.5 g of β-zeolite, 96.52 wt % of PTMEA-1782 and 3.48 wt % of $H_2O$, and the temperature was from 120 to 200° C. Overall, 1315 g of THF was collected with 95.7% purity.

Comparative Example 1

All operation parameters were the same as in example 1 except that the composition fed in the vessel included 2.5 g of mixture of $ZrO_2$ and $SiO_2$ (NISSAN GIRDLER CATALYST Co.) as a catalyst, and PTMEG-650, and the temperature was from 170 to 200° C. Overall, 880 g of THF was collected containing 3.7 wt % of $H_2O$.

Comparative Example 2

All operation parameters were the same as in example 1 except that the composition fed in the vessel included 1.8 g of ultra stable Y zeolite (USY zeolite; purchased from TOYO SODA) as a catalyst, and PTMEG-650, and the temperature was from 130 to 180° C. Overall, 2260 g of THF was collected containing 3.6 wt % of $H_2O$.

Comparative Example 3

All operation parameters were the same as in example 1 except that the composition fed in the vessel included 1.8 g of Y zeolite (purchased from CONTEKA) as a catalyst, and PTMEG-650, and the temperature was from 130 to 190° C. Overall, 850 g of THF was collected containing 3.4 wt % of $H_2O$.

The depolymerization yield of each catalyst used in the above examples is shown in Table 1.

TABLE 1

Comparison of depolymerization yield of each catalyst

|  |  | Composition | wt % | Catalyst | Temp. (° C.) | Yield* |
|---|---|---|---|---|---|---|
| PTMEG De-polymd. | Exp. 1 | PTMEG-650 | 100 | β-zeolite | 130–160 | 1527 |
|  | Exp. 2 | PTMEG-650 | 91.94 | β-zeolite | 130–170 | 1143 |
|  |  | $H_2O$ | 8.00 |  |  |  |
|  |  | NaCl | 0.05 |  |  |  |
|  |  | NaOAc | 0.01 |  |  |  |
| PTMEA De-polymd. | Exp. 3 | PTMEA-1782 | 100 | β-zeolite | 120–210 | 708 |
|  | Exp. 4 | PTMEA-1782 | 96.2 | β-zeolite | 120–200 | 877 |
|  |  | $H_2O$ | 3.8 |  |  |  |
| PTMEG De-polymd. | Comp. Exp. 1 | PTMEG-650 | 100 | $ZrO_2$—$SiO_2$ | 170–200 | 352 |
|  | Comp. Exp. 2 | PTMEG-650 | 100 | USY-zeolite | 130–180 | 1256 |
|  | Comp. 3 | PTMEG-650 | 100 | Y-zeolite | 130–190 | 472 |

*The yield is expressed as g-product/g-catalyst.

From the comparison shown in Table 1, the β-zeolite used as a catalyst shows excellent performance of depolymerization of polytetrahydrofuran derivatives. In addition to the depolymerization of PTMEG, the method of the invention can not only depolymerize the off-specification intermediate (e.g. PTMEA), but also depolymerize PTMEG in the presence of by-products or impurities such as water, sodium chloride, and sodium acetate. Moreover, the depolymerization yield of β-zeolite as a catalyst is superior to those in the prior art.

While the invention has been particularly shown and described with reference to the preferred embodiment thereof, it will be understood by those skilled in the art that various changes in form and details may be made without departing from the spirit and scope of the invention.

What is claimed is:

1. A method for depolymerization of a mixture comprising polytetrahydrofuran derivatives, comprising heating the mixture comprising polytetrahydrofuran derivatives in the presence of a β-zeolite catalyst at 100–250° C. to obtain tetrahydrofuran.

2. The method as claimed in claim 1, wherein the polytetrahydrofuran derivatives are selected from the group consisting of polytetramethylene ether glycols and polytetramethylene ether acetates.

3. The method as claimed in claim 2, wherein the mixture further comprises water, sodium chloride, and sodium acetate.

4. The method as claimed in claim 1, wherein the mixture is heated at 130–210° C.

5. A method for depolymerization of a mixture comprising polytetramethylene ether glycols, comprising heating the mixture comprising polytetramethylene ether glycols in the presence of a β-zeolite catalyst at 100–250° C. to obtain tetrahydrofuran.

6. The method as claimed in claim 5, wherein the mixture further comprises water, sodium chloride, and sodium acetate.

7. The method as claimed in claim 5, wherein the mixture is heated at 130–210° C.

8. A method for depolymerization of a mixture comprising polytetramethylene ether acetates, comprising heating the mixture comprising polytetramethylene ether acetates in the presence of a β-zeolite catalyst at 100–250° C. to obtain tetrahydrofuran.

9. The method as claimed in claim 8, wherein the mixture further comprises water.

10. The method as claimed in claim 8, wherein the mixture is heated at 130–210° C.

* * * * *